United States Patent [19]

Hungerford et al.

[11] Patent Number: 5,299,141

[45] Date of Patent: * Mar. 29, 1994

[54] AUTOMATIC FLUID MONITORING AND SAMPLING APPARATUS AND METHOD

[75] Inventors: William G. Hungerford; William D. Dickinson, both of Medina, N.Y.

[73] Assignee: American Sigma, Inc., Medina, N.Y.

[*] Notice: The portion of the term of this patent subsequent to Feb. 25, 2009 has been disclaimed.

[21] Appl. No.: 954,288

[22] Filed: Sep. 30, 1992

Related U.S. Application Data

[63] Continuation-in-part of Ser. No. 846,602, Mar. 5, 1992, and Ser. No. 612,832, Nov. 13, 1990, Pat. No. 5,172,332, which is a continuation-in-part of Ser. No. 455,981, Dec. 22, 1989, Pat. No. 5,091,863.

[51] Int. Cl.$^5$ .............................................. G01F 11/00
[52] U.S. Cl. ................................ 364/510; 73/863.01; 141/1; 422/82.11
[58] Field of Search .............................. 364/509, 510; 73/863.01, 863, 863.02, 863.03, 863.34; 141/1, 89, 91, 94, 130; 422/82.11, 98; 385/12

[56] References Cited

U.S. PATENT DOCUMENTS

| | | | |
|---|---|---|---|
| Re. 33,064 | 9/1989 | Carter et al. | 422/82.11 |
| 4,050,895 | 9/1977 | Hardy et al. | 422/98 |
| 4,710,353 | 12/1987 | Tanaka et al. | 422/82.11 |
| 4,846,548 | 7/1989 | Klainer | 385/12 |
| 5,091,863 | 2/1992 | Hungerford et al. | 364/510 |
| 5,095,514 | 3/1992 | Curtis | 385/12 |
| 5,096,671 | 3/1992 | Kang et al. | 385/12 |
| 5,156,927 | 10/1992 | Issachar | 422/82.11 |
| 5,172,332 | 12/1992 | Hungerford et al. | 73/863.01 |
| 5,176,882 | 1/1993 | Gray et al. | 385/12 |

Primary Examiner—Jack B. Harvey
Assistant Examiner—Ellis B. Ramirez
Attorney, Agent, or Firm—Irving M. Weiner; Joseph P. Carrier; Pamela S. Burt

[57] ABSTRACT

A fluid sampling apparatus provided as a unitary structure which automatically collects fluid samples according to modes of operation selected by a user, while monitoring an analyte of interest on a real-time basis on the basis of signals from a fiber optic sensor, and collecting and storing sampling and analyte data for later retrieval. The user may select from various modes of operation, including sampling triggered by a predetermined value(s) of the analyte, flow proportional sampling, and/or sampling at predetermined time intervals. The apparatus includes a self-contained microprocessor, together with associated program and data memory, for automatically controlling sampling operations, calculating analyte values on the basis of signals from the fiber optic sensor, calculating flow rate on the basis of signals from a flow sensing arrangement, and storing data relating to sample collection, analyte levels, and flow rate. The apparatus is further adapted to measure and store the actual discharge volume of the analyte loaded into a receiving fluid body, with the program memory being programmed to calculate loading values on the basis of flow rate values and analyte values as detected from any type of sensor capable of in situ real-time analyte measurement. Stored data can be called up on a display of the apparatus, or transferred to an external output device via a modem and telecommunication network or a portable data transfer unit.

31 Claims, 10 Drawing Sheets

AUTOMATIC FLUID MONITORING AND SAMPLING APPARATUS AND METHOD

This is a continuation-in-part of application Ser. No. 612,832 filed Nov. 13, 1990, which issued as U.S. Pat. No. 5,172,332, and which is in turn a continuation-in-part of application Ser. No. 455,981 filed Dec. 22, 1989 which issued as U.S. Pat. No. 5,091,863. This is also a continuation-in-part of application Ser. No. 846,602 filed Mar. 5, 1992.

BACKGROUND OF THE INVENTION

1. Field of the Invention

The present invention relates generally to an integrated automatic sampling and monitoring apparatus capable of automatically performing fluid sampling operations in conjunction with real-time, in situ monitoring of at least one analyte by means of at least one fiber optic sensor.

More particularly, the invention relates to a compact unitary fluid sampling apparatus having a computer control system operably connected with a fiber optic sensor so as to provide a user with various unique modes of operation. One unique mode of operation is the capability of triggering sampling operations on the basis of critical values of a given analyte, as measured by the fiber optic sensor. By thus limiting sample collection to upset conditions only, i.e., where a given analyte exceeds a predetermined critical value, the number of samples collected for subsequent laboratory analysis may be reduced so as to minimize analytical costs.

Other modes of automatic operation provided by the apparatus include sampling on the basis of time, and/or flow-proportional sampling based on flow rate. The apparatus also automatically stores sample collection data and measured values of an analyte(s) of interest. Real-time values of the analyte as measured by the fiber optic sensor can be viewed on an alphanumeric display of the apparatus, transferred to a remote computer, and/or retrieved from memory for transfer to an external output device such as a computer and/or a printer for producing a hard copy record.

The invention provides continuous in situ measurement of an analyte of interest, as measured by the fiber optic sensor, in a fluid discharge or stream. The output from the fiber optic sensor provides real-time values of the analyte, so that the collection of samples for later lab analysis may serve primarily as a back-up monitoring technique and may even be dispensed with entirely. The undesirable time lags necessitated by lab analysis of collected samples may thus be eliminated, with real-time measured values of an analyte serving to immediately alert a technician or other user to an upset condition.

The apparatus according to the invention also provides the unique capability of providing actual loading data, i.e., of measuring the actual quantity of an analyte in the form of a target pollutant discharged into a receiving channel or body of water. Quantitative assessment of actual loadings is performed by the computer control means on the basis of input from the fluid flow assembly of the apparatus and from the fiber optic sensor or any other type of sensor capable of providing in situ real-time measurement of an analyte. The resulting loading data is stored in memory. In addition, the apparatus is capable of averaging the values of a given analyte over time, with averaging data also being stored in memory.

The terminology "analyte" as used herein refers to any one of various physical and/or chemical properties of a fluid which may be measured by a fiber optic sensor for monitoring purposes and/or for triggering sampling operations. Such analytes include, but are not limited to, total suspended solids, total dissolved solids, total organic carbon, chloride, chemical oxygen demand, biochemical oxygen demand, nitrate, total phosphorus, ammonia nitrogen, nitrate, total Kjeldahl nitrogen, dissolved oxygen, oil and grease, total hydrocarbons, pressure, and a variety of other analytes of interest, such as various target pollutants including heavy metals.

The terminology "fiber optic sensor" as used herein refers to a sensor of the type having a fiber optic element which transmits light from a photoemitter to a photodetector, the fiber optic element comprising a fiber optic core made of highly light-transmissive optical fiber. Typically, the photoemitter takes the form of a light-emitting diode (LED). Light input to the fiber optic core by the LED traverses the core and becomes incident on the photodetector, which converts the modulated light into an electrical output signal which may be amplified for displaying or recording data. A sensing element, which is responsive to an analyte of interest, modifies the transmission properties of the fiber optic element, which in turn alters the output signals from the photodetector. Any one of a variety of types of fiber optic sensors may be employed with the invention, such as one in which the sensing element constitutes part of the fiber optic element itself, in the form of a clad surrounding the fiber optic core. The clad is made of material having a lower refractive index than that of the core, while at least a portion of the clad is made of a material responsive to an analyte of interest. The clad material is responsive to a given chemical(s) or other analyte, such that its refractive index changes in the presence of such analyte(s) to thereby alter the light-transmitting properties of the sensor. The analyte-sensitive clad material may be sensitive to a group of analytes, such as total heavy metals, total petroleum, or the like.

2. Description of the Relevant Art

In today's climate of deep concern over environmental pollution, municipal agencies and private companies alike are faced with the responsibility of carefully monitoring fluid waste, particularly in order to comply with stringent statutory and regulatory pollution limits or to conduct pollution research. To this end, an automatic fluid sampling apparatus is commonly used to repeatedly collect samples for subsequent laboratory analysis. In addition, a separate analytical meter may be used for on-site monitoring of a critical fluid parameter, such as pH level, to alert the user to an upset in the process stream. A separate flow meter may also be used for monitoring the volume of fluid flow and for pacing sampling operations in proportion to flow rate. The sampler, analytical meter and/or flowmeter are regularly transported for positioning in municipal or industrial manholes to monitor sewer lines containing fluid waste, or to remote field sites for monitoring, research purposes, or the like.

Various problems arise in using separate sampler, flowmeter and analytical devices at a remote field site or in a sewer manhole. Transporting a number of separate devices to a sampling site is cumbersome and inconvenient, while mounting of the separate devices in a manhole presents additional difficulties. The close confines of the manhole severely restricts manipulation of the devices, so that positioning and mounting of the separate devices often proves difficult, and sometimes impossible. Further, it is important that a record be kept of sample collection and other data in order to comply with federal and state requirements. With prior known sampler and meter devices, the only means by which such a record can be obtained is by recording the data by hand when it appears temporarily on a display of the device. This limitation leads to inaccurate or incomplete records at best.

The apparatus disclosed in U.S. Pat. No. 5,091,863 issued Feb. 25, 1992 overcomes problems associated with using separate samplers and flow meters by providing an integrated, compact automatic liquid sampling and flow measuring apparatus capable of pacing sampling in proportion to flow rate, and of storing sample collection and flow data for retrieval in hard copy form. On the other hand, U.S. Pat. No. 5,172,332 discloses an integrated automatic sampling and monitoring apparatus which overcomes the problems associated with separate automatic sampler and analytical meter devices. By combining a sampler and analytical meter, and a flowmeter if desired, in a unitary compact structure, the size and weight of the equipment is reduced while transport to remote sites and mounting in limited spaces is facilitated. The sampler and meter(s) share the same microprocessor, digital display, keyboard, circuitry, etc. The computer control means of the apparatus automatically calculates a fluid condition(s), such as pH level, and controls sampling operations on the basis of time, the fluid condition(s), and/or flow rate. The apparatus also stores sample collection and fluid condition(s) data, with access thereto being had either via an alphanumeric display or a portable unit for retrieving and transferring the data to a remote device such as a computer or a conventional printer from which a hard copy of the data may be obtained. The disclosures of U.S. Pat. Nos. 5,091,863 and 5,172,332 are both incorporated herein by reference thereto.

The present invention combines the unique capabilities of the foregoing apparatus with the desirable real-time measuring capabilities of fiber optic sensors. The apparatus according to the invention includes an integral operating unit comprising a fluid sampling assembly, a fluid flow sensing assembly, computer control means, and power means integrally combined in a compact unitary case. At least one fiber optic sensor is operably connected with the integral operating unit such that output signals therefrom are used to trigger sampling operations and/or to monitor real-time values of an analyte of interest. Measured values of the analyte may be viewed on a display of the apparatus, may be transmitted to a remote location, and/or may be stored in memory for later retrieval.

SUMMARY OF THE INVENTION

The invention provides an apparatus for automatically collecting samples from a fluid stream and for monitoring at least one analyte in the stream on a real-time basis, according to at least one mode of operation selected by a user. The apparatus includes means for controlling the apparatus, a fluid sampling assembly having an inlet for receiving fluid from the stream, and power means for supplying power to each element of the apparatus, with the fluid sampling assembly, control means and power means comprising an integral operating unit disposed within a single case. The apparatus further comprises a fiber optic sensor for detecting values of the analyte in the fluid stream and for outputting signals related thereto, the fiber optic sensor being selectively connected to an input connection of the integral operating unit. The control means of the apparatus comprises a microprocessor, program memory and data memory. The program memory is programmed for computing values of the analyte. The microprocessor receives the signals related to the analyte via the input connection and utilizes the program memory to calculate values of the analyte based on the signals. The at least one mode of operation which may be selected by the user includes a first mode of operation in which sampling is triggered by at least one predetermined value of the analyte being monitored. The data memory stores user-selected input parameters including operating mode selection data and the predetermined value of the analyte. The microprocessor controls the fluid sampling assembly according to the at least one mode of operation selected by the user, based on a deviation of computed values of the analyte from the user-selected predetermined value of the analyte. The data memory stores fluid sampling data and analyte data.

It is an object of the invention to provide an automatic sampling apparatus which monitors at least one analyte of interest on a real-time basis by means of a fiber optic sensor, and which automatically triggers sampling operations on the basis of at least one predetermined value of the analyte as selected by the user.

In a preferred embodiment, the apparatus also automatically collects samples according to second and third modes of operation selected by the user. In the second mode of operation, sampling is initiated on the basis of time, the user-selected input parameters stored by the data memory include sampling times. In the third mode of operation, sampling is initiated on the basis of flow rate, with the apparatus being provided with flow sensing means for outputting signals related to fluid flow in the stream, the flow sensing means being selectively connected to a second input connection of the integral operating unit, and the user-selected input parameters stored by the data memory including at least one fluid flow-related parameter.

According to a further object of the invention, the apparatus is also adapted to measure the actual discharge volume of the analyte loaded from the fluid stream into a receiving fluid body. The program memory is programmed for computing flow rate values, and for calculating loading values on the basis of the analyte values and flow rate values. The microprocessor receives the signals related to fluid flow via the second input connection and utilizes the program memory to calculate flow rate values. The microprocessor utilizes the program memory to calculate loading values of the analyte on the basis of calculated analyte values and flow rate values, and the data memory stores loading data.

A further object of the invention is to provide for transfer of data stored in the data memory of the apparatus to an external output device which may be located at a remote location. To this end, the apparatus may be provided with a conventional modem adapted to transfer data via a telecommunication network to a remote external output device. Alternatively, a portable data transfer unit provided with its own microprocessor may be connected to the apparatus to retrieve data therefrom for transfer to an external output device.

The above and further objects, details and advantages of the invention will become apparent from the following detailed description, when read in conjunction with the accompanying drawings.

DETAILED DESCRIPTION OF PREFERRED EMBODIMENTS

Figure 1:
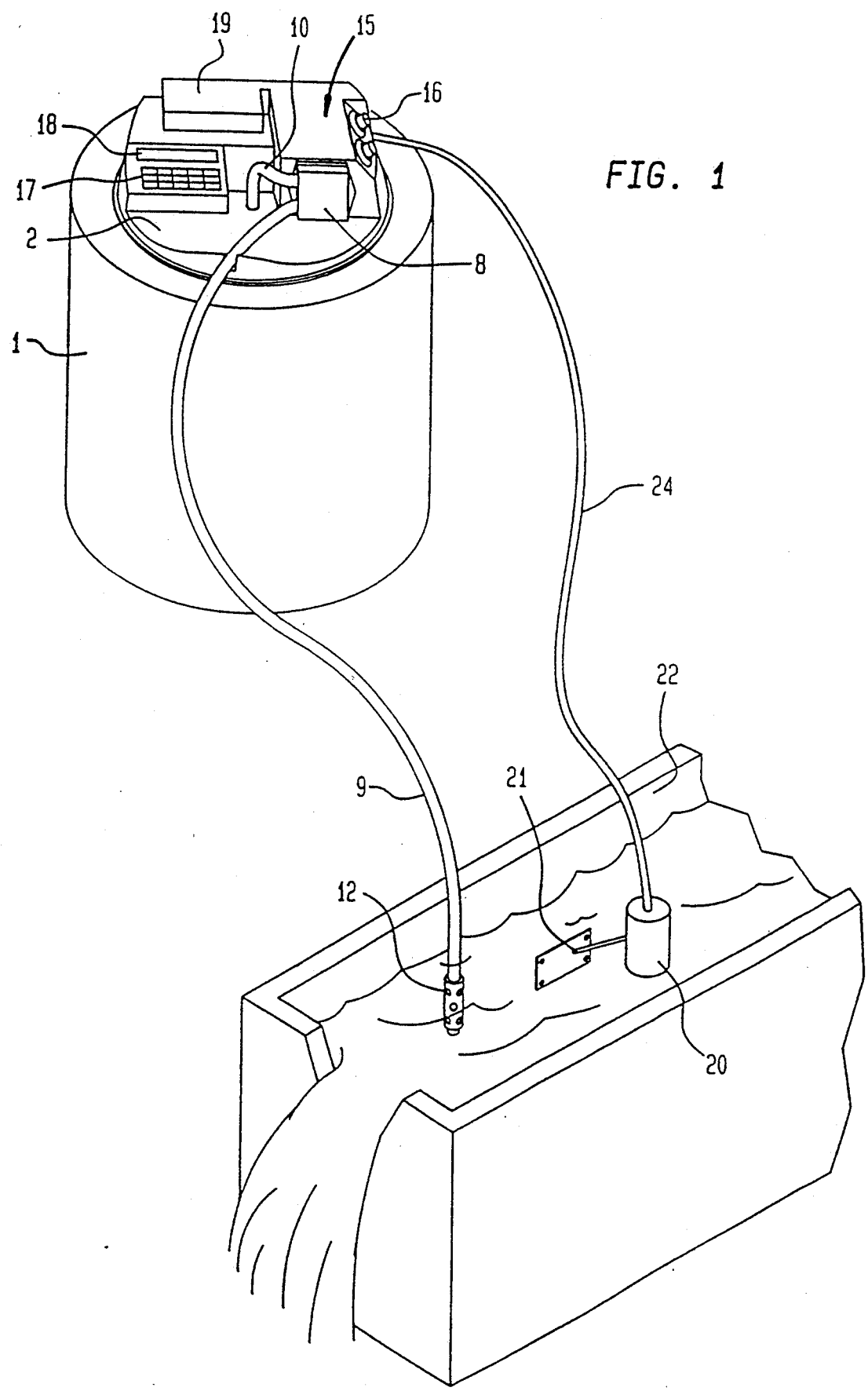
FIG. 1 is a perspective view of an automatic fluid sampling and analyte monitoring apparatus according to a preferred embodiment of the invention.
Figure 2:
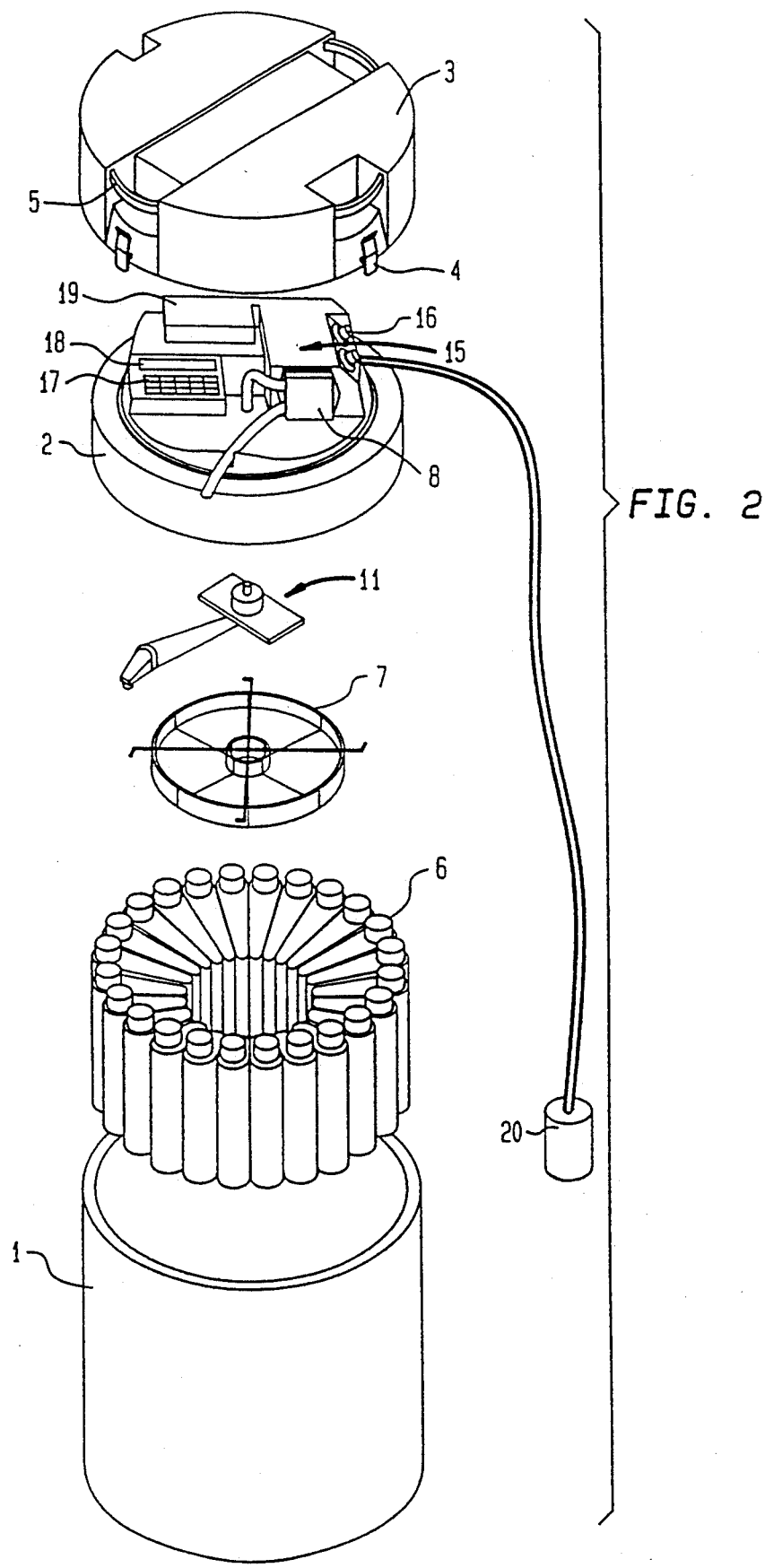
FIG. 2 is a disassembled view of the apparatus of FIG. 1, including multiple discrete sample containers.
Figure 3:
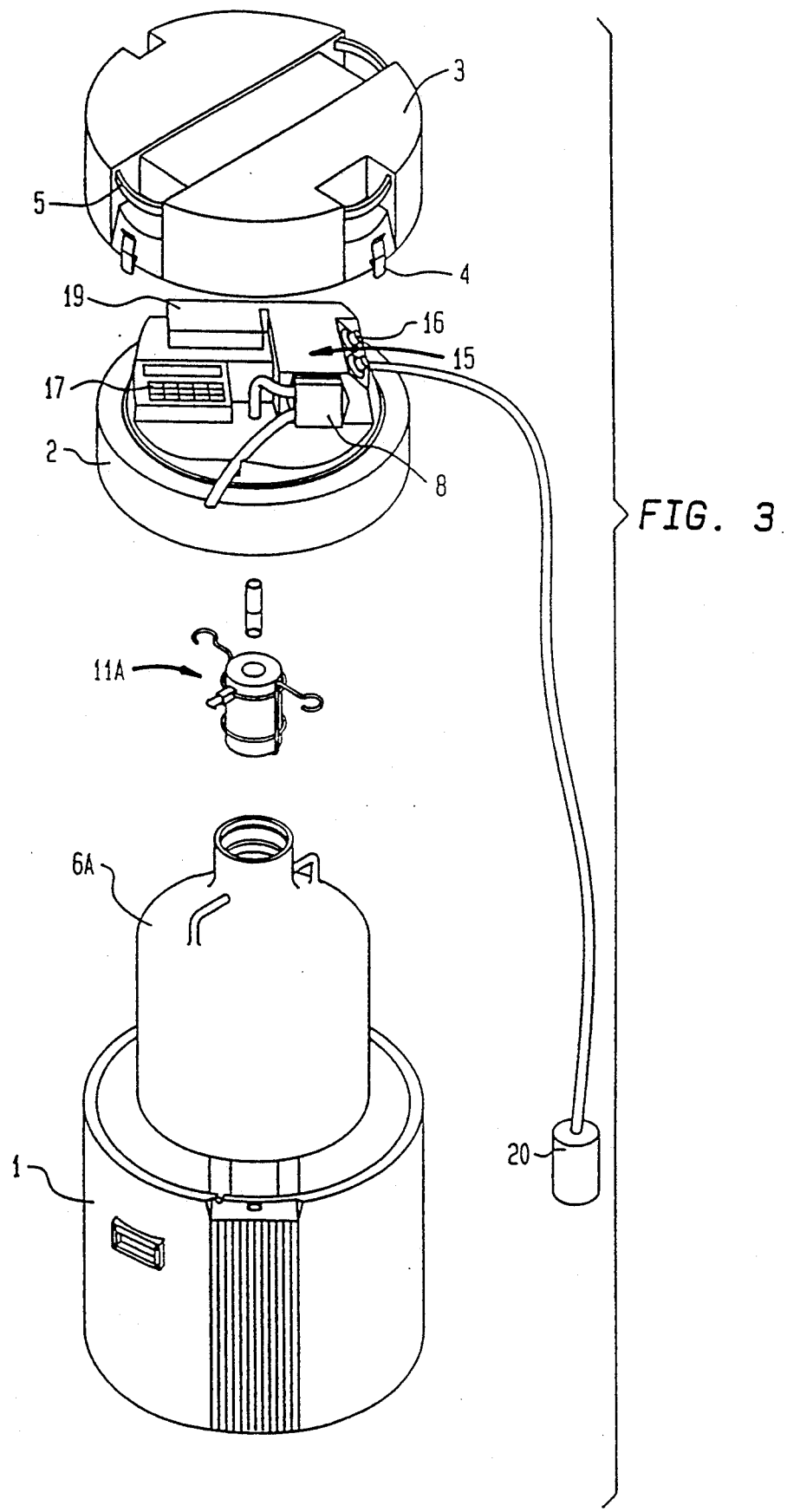
FIG. 3 is a disassembled view of the apparatus of FIG. 1, similar to FIG. 2, except that the multiple sample containers are replaced by a single composite sample container.

FIGS. 1-3 generally depict an automatic fluid sampling and monitoring apparatus according to a preferred embodiment of the invention. The apparatus includes a case comprising a lower portion 1 for holding one or more sample containers, an upper component supporting portion 2 and a top cover 3. Each portion of the case is preferably fabricated of a rugged thermoplastic material, such as ABS plastic or molded polyethylene, which is impact resistant and capable of withstanding the stresses of mounting and use in a sewer manhole. The upper component-supporting case portion 2 is adapted to be substantially tightly received in the upper end of lower case portion 1, and the top cover 3 is removably received over upper case portion 2 to protectively enclose the components supported by case portion 2, and to close the case. Top cover 3 is provided with a plurality of fasteners 4 adapted to mate with fastening portions provided at the upper outer surface of lower case portion 1, and handles 5 for ease of transport of the apparatus.

The lower case portion 1 is shown in FIG. 2 as accommodating therein a plurality of sample containers 6. Lower case portion 1 is preferably double-walled with approximately 1" of insulation, for example, to insulate the interior thereof for storing ice to keep sample containers cool. The sample containers 6 are shown in the form of 24 one-liter bottles made of polyethylene or glass, for example. It is to be understood, however, that any number of sample containers ranging from only one to a multiplicity thereof may be employed. Sample containers 6 are supported in a generally circular array.

In a modification shown in FIG. 3, a single large composite sample container 6A is accommodated in lower case portion 1 rather than the plurality of containers 6 shown in FIG. 2.

The fluid sampling assembly of the invention may take any desired form of liquid sampler capable of automatic control by a microprocessor to take repeated accurate samples. A sampler having desired characteristics is described in U.S. Pat. No. 4,660,607 issued in 1987 to Griffith et al, the disclosure of which is incorporated herein by reference thereto.

The fluid sampling assembly employed in preferred embodiments of the present invention may be substantially similar to that disclosed in U.S. Pat. No. 4,660,607, and thus only a general description thereof is set forth herein. The assembly includes a reversible, positive displacement pump 8 mounted in casing portion 2 and having the inlet thereof selectively connected to a suitable length of sample intake conduit 9. Provided at the lower intake end of conduit 9 is a weighted strainer member 12 which holds the end of the conduit under water and prevents large objects from entering and blocking the conduit. The upper intake end of conduit 9 is connected to a fluid detection sensor. A second length of conduit 10 is connected to the opposite end of the fluid detection sensor, and through pump 8 to an electro-mechanical distributor mechanism 11 for routing fluid samples to any of the containers 6. A positioning insert 7 is provided between the distributor mechanism 11 and the tray holding sample containers 6. For the single sample container 6A shown in FIG. 3, the positioning insert 7 and distributor mechanism 11 are replaced by a sample directing member 11A.

The pump 8 is cyclically operated in a reverse purging direction or a forward sample drawing direction depending on signals supplied by processing means incorporated in the computer control means of the present invention, described in detail below. The processing means determines the rate of fluid flow and the time the pump must operate to fill all the tubing plus a desired sample volume, on the basis of signals from a fluid detection sensor disposed upstream of the pump 8, and user programmed data relating to the tubing 9. Pump 8, although described by way of example as a positive displacement pump, may alternatively comprise any other suitable type of pump, such as a vacuum pressure pump, etc.

As shown in FIGS. 1 and 2, case portion 2 also supports computer control means 15, and a plurality of external connectors 16 providing access to computer control means 15. Also supported by case portion 2 is a user-input keypad 17, an alphanumeric display 18 and power supply means 19 which may take the form of a rechargeable battery and/or a power pack for alternatively supplying power to the apparatus from an external AC power source. The aforesaid components supported by case portion 2 are mounted in a watertight manner for protection from adverse external conditions. Additional protection of such components is afforded by fastening top cover 3 in position, although even without top cover 3 the case with the components mounted therein is submersible, watertight, dust-tight, corrosion resistant and ice resistant (e.g., NEMA 4x, 6).

Selectively connected to the computer control means of the invention, via one of the external connectors 16, is a sensor means 20 for in situ measuring of real-time values of a given analyte(s) in a fluid discharge or stream.

Figure 4:
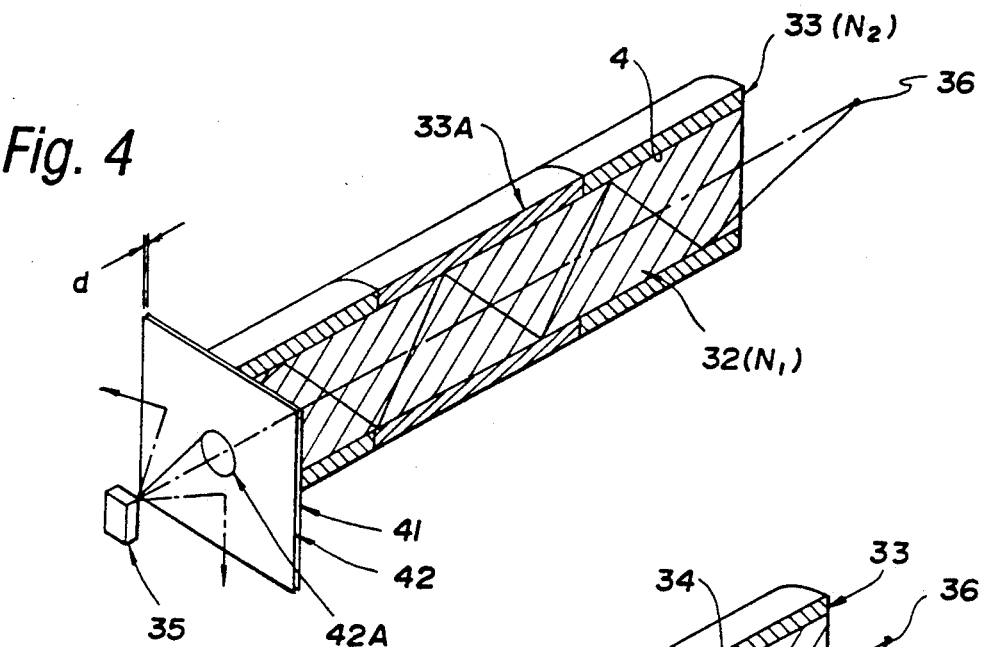
FIG. 4 depicts a first embodiment of a fiber optic sensor for use with the invention, the sensor including an aperture stop and field stop for focusing light to the core and eliminating the input of light to the clad, respectively, of the sensor.

As shown in FIGS. 4–11, the sensor means 20 of FIG. 1 is preferably a fiber optic sensor of the type disclosed in co-pending U.S. patent application Ser. No. 846,602. With reference to FIG. 4, the sensor has a fiber optic core 32 constructed of a short length of glass fiber, such as silica fiber, having a diameter of approximately 1 mm or less, and a length of approximately 50 mm or less. Surrounding the core is a clad 33 including a portion 33A made of a sensing material which is responsive to a chemical or analyte of interest, the clad 33, 33A typically having a depth of approximately 20 microns or less. The core 32 has a refractive index $N_1$ which is greater than the refractive index $N_2$ of the clad 33. As such, when light is input to the fiber optic core 32 from a light source or LED 35, light which is incident on the core-clad boundary interface 34 at a critical angle or greater (described below) will be totally internally reflected and transmitted along the core 32. However, when the sensor is in the presence of a chemical or analyte to which the clad portion 33A is particularly adapted to be responsive, the refractive index of clad portion 33A changes so that the amount and angles of light internally reflected from the core-clad interface 34 also changes. The resulting change in light transmission along core 32 in turn results in a change in the intensity and/or angle of light signals detected by photodetector 36, which change may be correlated to a known relationship between the analyte of interest and the clad.

An important characteristic of the fiber optic sensors shown in FIGS. 4–11 is that they eliminate the destabilizing effect of clad light, i.e., the reflection and refraction of light rays input to the clad by the photodetector and independently propagated along the clad so as to undesirably interfere with transmission of light through the core. To this end, the fiber optic sensors in FIGS. 4–11 are each provided with a field stop and/or clad light stop means suitably arranged relative to the core 32, the clad 33, and the LED 35 or photodetector 36 so as to eliminate the deleterious effect of clad light and enhance the stability and reliability of the fiber optic sensor. In addition, to optimize the transmission of light through the core 32, aperture stop means may be provided between the LED 35 and the fiber optic core 32 to focus the conical radiation pattern from the LED onto the fiber optic core.

In FIG. 4, the destabilizing effect of clad light is eliminated by field stop 41 which is disposed between the LED 35 and the fiber optic element. The field stop 41, which is arranged adjacent to and behind an aperture stop member 42, comprises a flat member formed of a light-obstructing material and having a large central aperture 41A (FIG. 5) with a diameter which is substantially equal to or less than the diameter of the fiber optic core 32, while peripheral portions of field stop 41 entirely shield the light-receiving end of clad 33 from light. The transmission of light through core 32, as well as the output signals from photodetector 36, are thereby stabilized.

The aperture stop 42 comprises a flat member made of a light-obstructing material and having a central aperture 42A. The aperture stop 42 is positioned between LED 35 and field stop 41, however, aperture stop 42 can be used independently of field stop 41 by positioning same between LED 35 and the light-receiving end of the fiber optic element. If desired, aperture stop 42 and field stop 41 can be formed integrally as a single member, and neither is limited to the illustrative rectangular shapes shown. The size of aperture 42a of aperture stop 42 controls the size of the bundle of light rays input to core 32, the diameter of aperture 42a being less than that of core 32. The size of aperture 42a may be varied to compensate for a number of variables. For example, the diameter of aperture 42a may be made smaller where aperture stop 42 is disposed a distance from the end of the fiber optic element, and larger where aperture stop 42 is disposed relatively close to or adjacent the end of the fiber optic element. Moreover, the size of aperture 42a may be varied to compensate for variations in the initial output signals from different fiber optic elements.

Figure 5:
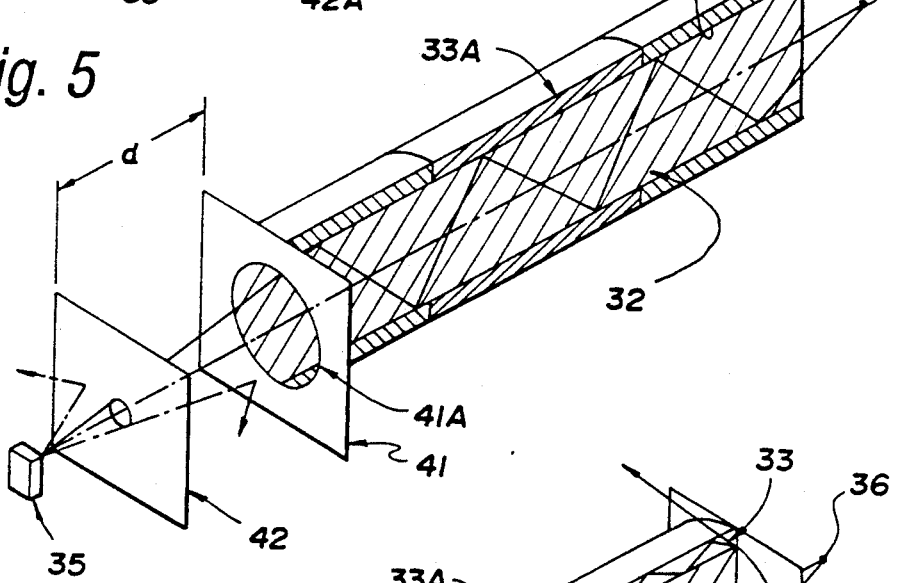
FIG. 5 shows a second embodiment of a fiber optic sensor for use with the invention, in which the aperture stop and field stop are separated.

In FIG. 5, the field stop 41 and aperture stop 42 are separated, with aperture stop 42 being relatively closer to LED 35 than aperture stop 41. The relative distances between the LED 35, aperture stop 42 and field stop 41, as well as the diameter of aperture 42A, can be varied as necessary to obtain optimal light transmission through core 32.

Figure 6:
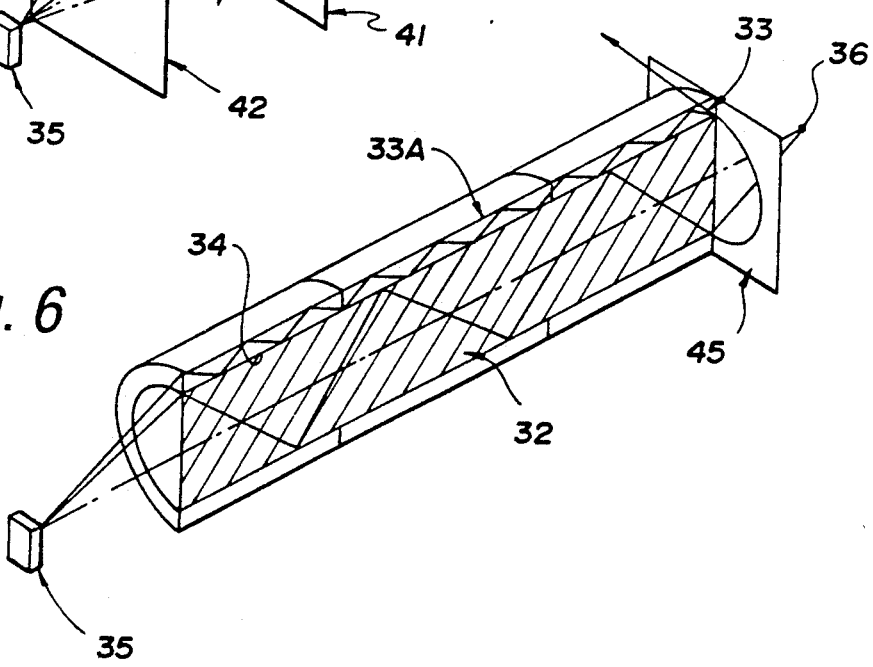
FIG. 6 depicts a third embodiment of a fiber optic sensor for use with the invention, employing a clad light stop diaphragm at the light-emitting end of the fiber optic element to prevent clad light from reaching the photodetector.

In FIG. 6, the field stop 41 is replaced by a clad light stop diaphragm 45 at the light-emitting end of the fiber optic element. The structure of diaphragm 45 is similar to that of field stop 41, serving to effectively shield the light-emitting end of clad 33. By positioning diaphragm 45 between the light-emitting end of the fiber optic element and the photodetector 36, clad light which has propagated along clad 33 is completely obstructed from photodetector 36 such that no clad light is incident on photodetector 36. This embodiment may be desirable for fiber optic sensors in which the clad light phenomenon may have advantageous effects on overall functioning, while the deleterious interference effect of clad light otherwise incident upon photodetector 36 is prevented by diaphragm 45. If desired, diaphragm 45 may be employed at the light-emitting end of the fiber optic element in conjunction with field stop 41 at the light-receiving end.

Figure 7:
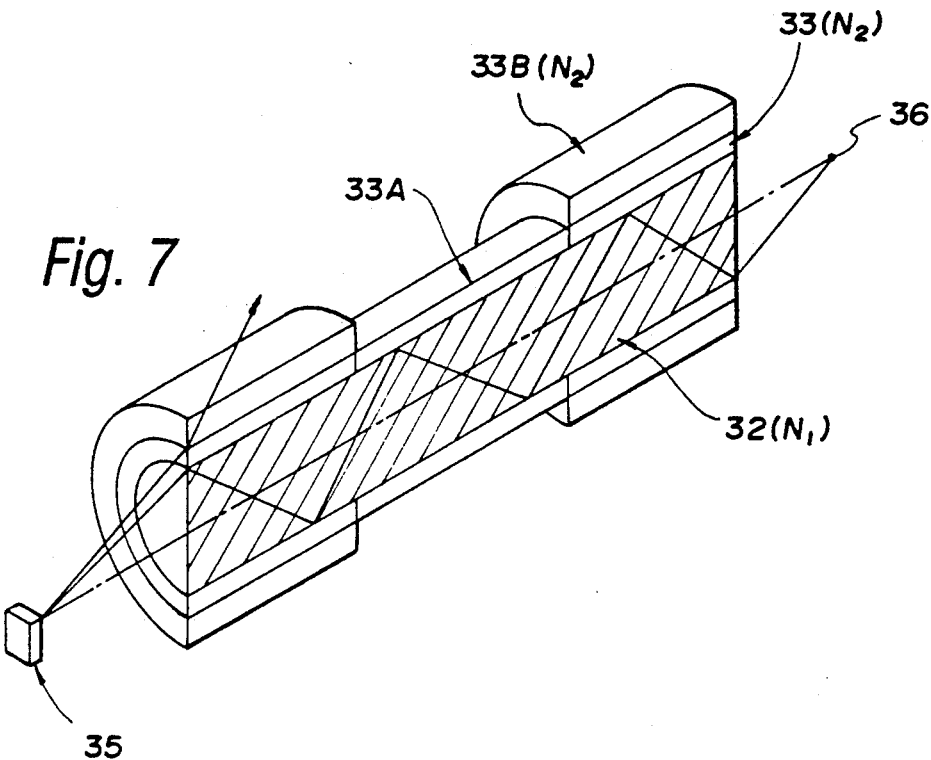
FIG. 7 illustrates a fourth embodiment of a fiber optic sensor for use with the invention, in which supplemental clad portions having the same index of refraction as that of the main clad are employed to mitigate the effects of clad light.
Figure 8:
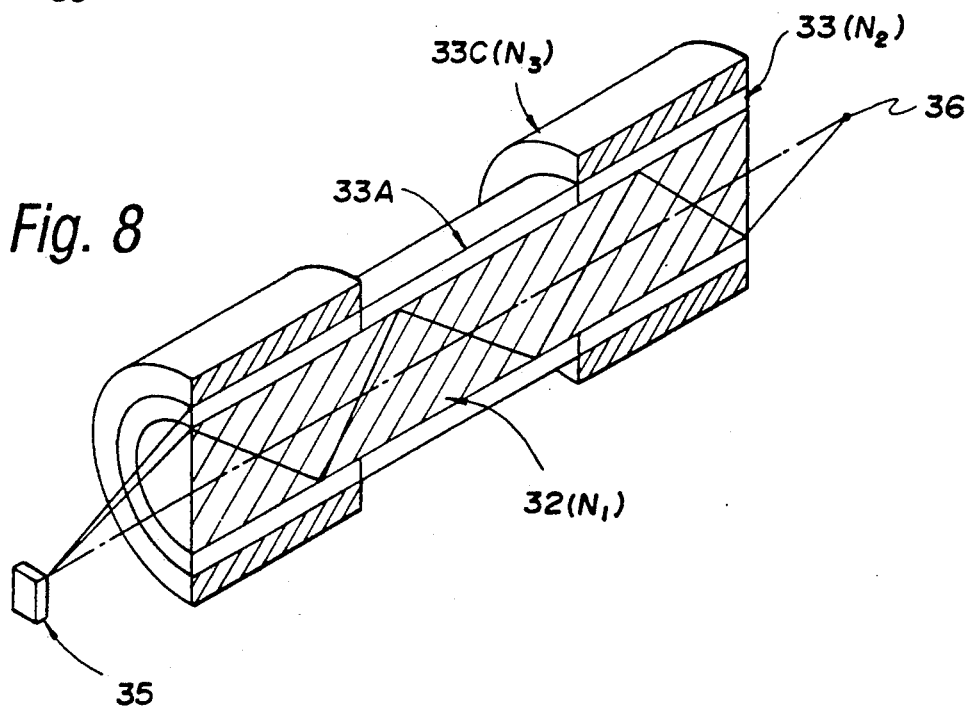
FIG. 8 shows a fifth embodiment of a fiber optic sensor for use with the invention, in which supplemental clad portions having a higher index of refraction than that of the main clad are employed to mitigate or eliminate clad light.

In the sensor shown in FIG. 7, the means for eliminating or mitigating the destabilizing effect of clad light on core light transmission takes the form of supplemental clad portions 33B provided so as to surround the clad 33 in all but the area of analyte-responsive portion 33A. Supplemental clad portions 33B are made of a material having a refractive index $N_2$ matched to that of the clad 33, and may be made of the same material as clad 3. The sensor shown in FIG. 8 is similar to that of FIG. 7, except that the supplemental clad portions 33C are formed of a material having a higher index of refraction N3 than that of the clad 33 (N2).

Figure 9:
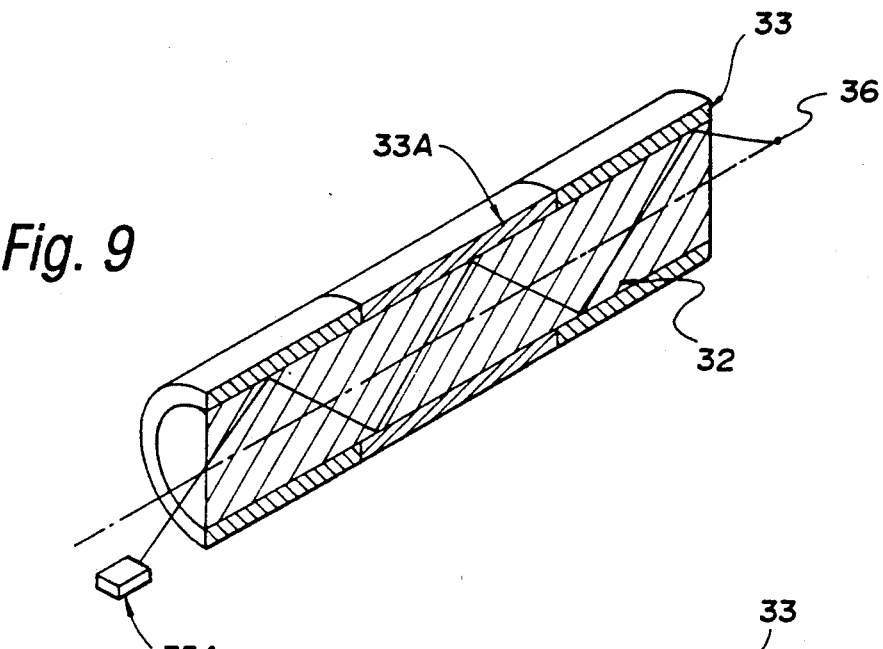
FIG. 9 depicts a sixth embodiment of a fiber optic sensor for use with the invention, employing an edge-type LED light source to mitigate clad light.
Figure 10:
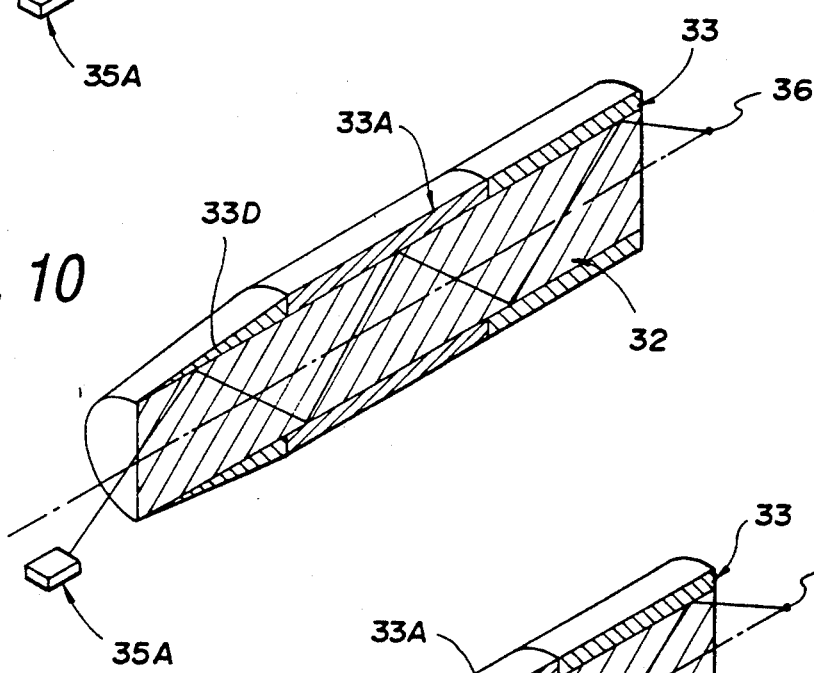
FIG. 10 illustrates a seventh embodiment of a fiber optic sensor for use with the invention, in which a tapered-end clad portion is combined with an edge-type LED light source to mitigate or eliminate clad light.
Figure 11:
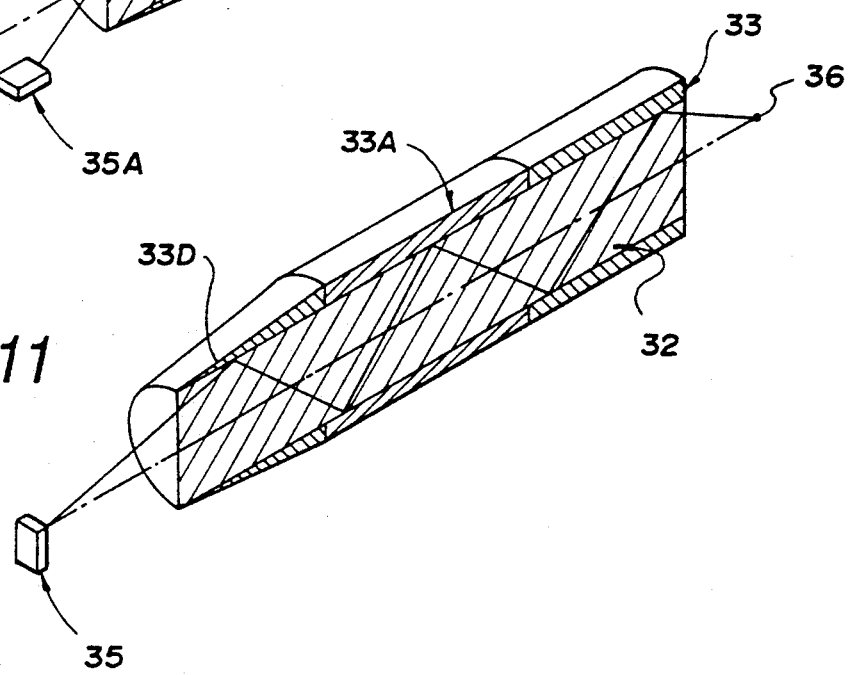
FIG. 11 depicts an eighth embodiment of a fiber optic sensor for use with the invention, in which a tapered-end clad portion is employed with a surface-type LED light source to mitigate clad light.

The sensor shown in FIG. 9 includes an LED 35 of an edge-source type, in which light is emitted from an edge portion of the LED, whereby the input of light to the clad is mitigated or substantially eliminated by virtue of the more focused input of light to core 32. FIG. 10 depicts a sensor employing the edge-source type LED 35A of FIG. 9 in combination with a tapered clad portion 33D at the light-receiving end of the fiber optic element. There thus remains essentially no clad material to which the focused light from the edge-source LED 35A can be input, thus eliminating the phenomenon of clad light. FIG. 11 depicts an embodiment employing the tapered clad portion 33D of FIG. 10, and substituting a surface-source type LED 35 for the edge-source type employed in FIG. 10. In FIG. 11, even though light from the surface-source type LED 35 is relatively less focused than that from an edge-source type LED, the elimination of clad material from the light-receiving end of the fiber optic element ensures that no light will be input to the clad.

It will be understood from the foregoing that a principal feature of the sensors shown in FIGS. 4-11 is the elimination and/or control of the destabilizing effect of clad light, independently input to and propagated along the clad, on the transmission of light through the fiber optic core. Various means other than those shown may be used to this end, such as the application of a light-obstructing coating material directly to the end of the clad to cover same. Likewise, the clad light stop diaphragm 45 of FIG. 6 may be replaced by a coating of light-obstructing material applied directly to the light-emitting end of the clad. Similarly, the tapered clad portion 33D described with reference to FIGS. 10 and 11 may also be provided at the light-emitting end of the fiber optic element.

The second principal feature of the sensors shown in FIGS. 4-11 is the aperture stop means provided at the light-receiving end of the fiber optic element. If desired, the aperture stop means and the field stop means may take the form of a single unitary member interposed between the LED and the light-receiving end of the fiber optic element to simultaneously focus light on the core 32 while shielding the clad 33 from any light input. The aperture stop means may also be employed independently of the field stop means by arranging the aperture stop some distance from the light-receiving end of the fiber optic element. In such an arrangement, the diaphragm 45 may for example be employed at the light-emitting end of the element to prevent clad light from reaching the photodetector.

While it is contemplated that the fiber optic sensor 20 for use in connection with the various embodiments of the invention is preferably of the type described with reference to FIGS. 4-11, it is not limited thereto. Other types of sensors are also suitable for use with the invention, such as, for example, a reservoir type fiber optic sensor in which the sensing element comprises a reagent which interacts with an analyte of interest, the reagent being disposed at the tip of the optical fiber. It is further contemplated that the sensor 20 may comprise a sensor package containing a plurality of fiber optic sensors, each responsive to a different analyte of interest.

As shown in FIG. 1, the sensor 20 and the end of sample intake conduit 9 may be directly positioned in any fluid stream, such as, for example, in a gravity fed fluid channel, such as an open flowing sewer passage, or in a pressurized fluid line. By way of example, FIG. 1 shows the sensor 20 positioned in a fluid flow restricting device 22 in the form of a V-notch weir. Sensor 20 may also, if desired, be conveniently positioned in other flow restricting devices such as various types of flumes, weirs or nozzles. Electrical output signals from the photodetector 36 of sensor 20 are conveyed, via cable 24, from sensor 20 to the computer control means of the invention as described below. Cable 24 also serves as a means for supplying electrical current from power supply means 19 to the sensor 20.

The computer control means of the invention, and the interface means for connecting a fiber optic sensor thereto, will be described in detail with reference to FIG. 12. The boxes labelled "A/D (Analog to Digital) Converter" and "Signal Conditioning Electronics" shown to the right of the dashed line in FIG. 12 together define the means for interfacing the fiber optic sensor with the microprocessor. The interface means includes electronic circuitry, with amplifiers, and an analog to digital converter provided on a single board which is integrally connected with the computer control means. The signal conditioning electronics of the interface means amplifies the voltage from the fiber optic sensor 20 to a voltage signal of suitable amplitude for the A/D converter. The A/D converter translates the voltage output from the signal conditioning electronics to a binary number which may then be processed by the microprocessor of the computer means.

Figure 12:
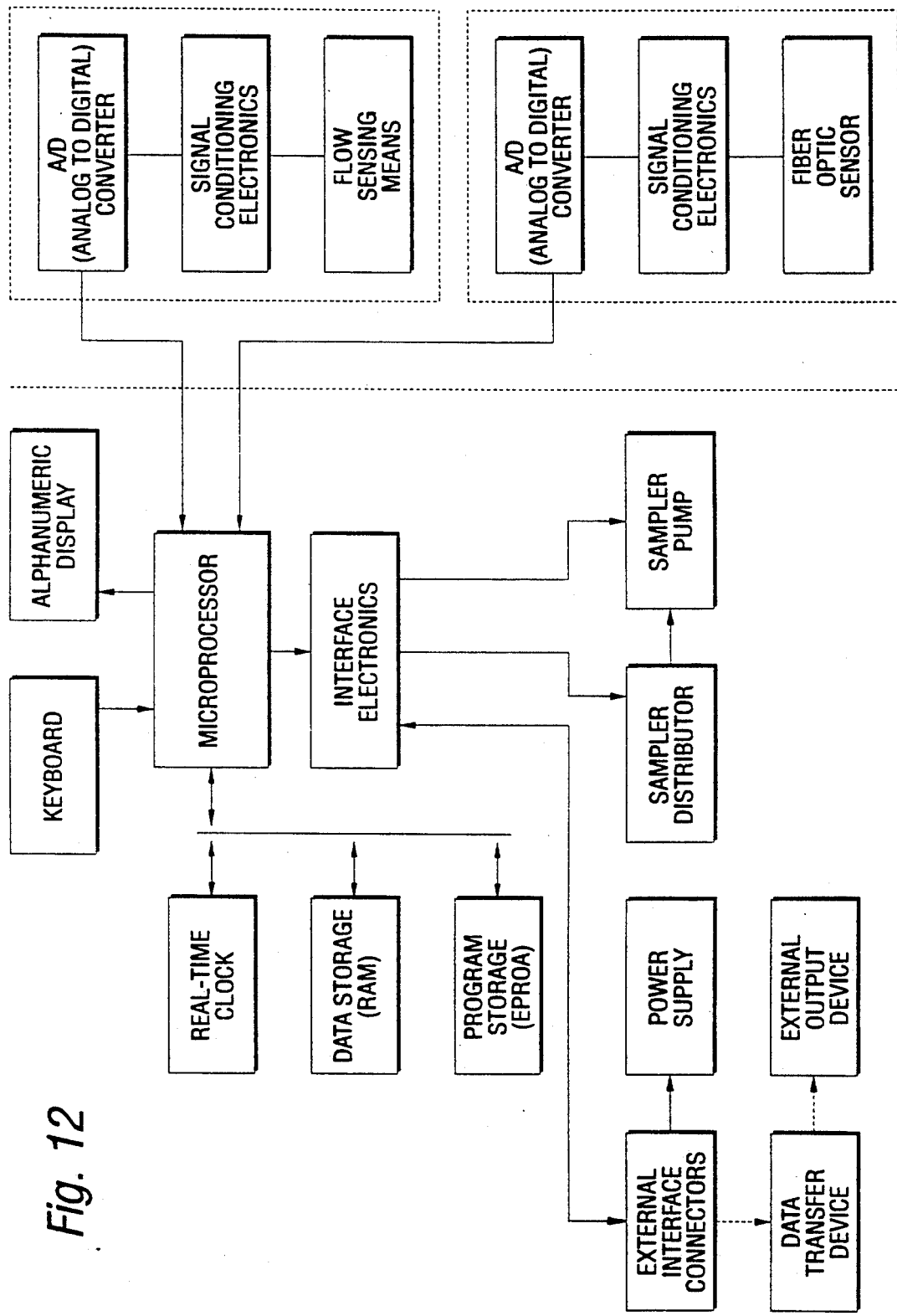
FIG. 12 is a block diagram of the various components of the apparatus according to the invention, as controlled by the computer control means.

Also shown to the right of the dashed line in FIG. 12 is a fluid flow sensing assembly including a flow sensing means for detecting a variable related to fluid flow and outputting a signal proportional thereto. The flow sensing means may take the form of any desired suitable flow sensor, such as, for example, a pressure transducer type sensor, an ultrasonic type sensor, a float type sensor, etc., mounted in an operable position relative to a fluid channel as described in U.S. Pat. No. 5,091,863. Interface means, including an A/D converter and signal conditioning electronics, are provided on a single board which is integrally connected with the computer control means. The interface means functions to provide a precision voltage level to the flow sensor, and to detect signals from the flow sensor. The detected signals are amplified and smoothed (filtered for noise), and then converted to digital form by the A/D converter for input to the computer control means. The program storage memory of the microprocessor is provided with flow measuring programming, described in detail below, which allows the microprocessor to calculate the flow rate on the basis of processed signals received from the flow sensing assembly, and to record calculated flow rate data. The user can set the desired flow recording interval as desired, and is also offered the opportunity to calibrate the flow sensor.

The apparatus of FIG. 12 has the capability of controlling sampling operations on the basis of time and/or predetermined value(s) of an analyte(s) of interest, as well as the capability of controlling sampling operations in proportion to calculated flow rate, i.e., on the basis of flow intervals selected by the user. The user may access stored data relating to the sampler program, flow rate and/or the given analyte(s) being monitored by requesting either that it be displayed on alphanumeric display 18 or transmitted to a remote computer for analysis, permanent storage or obtaining a hard copy. Because the sampling assembly, fluid flow sensing assembly and fiber optic sensor interface means share a common computer control means, a very versatile apparatus having each of the foregoing capabilities may be provided as a compact unitary structure.

As shown to the left of the dashed line in FIG. 12, the apparatus according to the invention includes a microprocessor which performs all mathematical and control functions required to operate the apparatus, a keyboard (keypad 17 in FIG. 1) which permits the user to program the apparatus and monitor its operation, and a real-time clock. The real-time clock provides the microprocessor with access to current time and date information, so that events occurring during program execution may be recorded with corresponding time and date of occurrence. As described below, the microprocessor according to the invention includes both program storage memory and data storage memory.

PROGRAM STORAGE MEMORY

The program storage memory is preferably provided in the form of pre-installed firmware in read-only memory, such as programmed EPROM chips, which control operation of the microprocessor.

The program storage memory (EPROM) of the microprocessor according to the invention implements all of the functions required to operate the sampler pump and distributor, operate the alphanumeric display and keypad, store and retrieve data obtained during execution of a sampling program, read and process signals from the flow sensing assembly, and read and process signals from the fiber optic sensor 20.

The program storage memory (EPROM) of the microprocessor includes the following programming, each of which will be described in detail:
Interface Programming;
Sampling Assembly Programming;
Flow Measuring Programming; and
Fiber Optic Sensor Signal Programming.

The Interface Programming allows the microprocessor to control the user input keypad 17, alphanumeric display 18, the real-time clock, and the interface and signal conditioning electronics used by the sampling programming to access the pump and distributor.

The Sampling Assembly Programming allows the microprocessor to control the sampling assembly by implementing user-programmed parameters stored in the data storage memory. The sampling assembly programming includes algorithms using real time, elapsed time, fluid flow rate, and/or analyte value information to collect fluid samples using the sampler pump and the distributor mechanism. Operation of this programming is controlled by user-programmed parameters, described below with reference to the data storage memory.

The Flow Measuring Programming comprises firmware which allows the microprocessor to calculate the fluid depth and flow rate on the basis of processed signals received from the flow sensing assembly. The programming includes depth vs. flow equations which characterize the relationship between the "head" and flow rate for various types and sizes of fluid flow restricting devices. Floating point math algorithms are provided to enable the microprocessor to perform high precision mathematical operations required to accurately calculate the values of fluid flow-related variables, such variables comprising the fluid depth which is calculated from the output of the submerged flow sensor, and the fluid flow rate which is calculated from the measured fluid depth. Algorithms are included for performing addition, subtraction, multiplication, division, exponentiation, logarithms and trigonometry functions to a precision equivalent to over four significant figures.

The Fiber Optic Sensor Signal Programming comprises firmware which allows the microprocessor to receive processed signals from the fiber optic sensor interface means and to record data in the form of measured analyte concentration values. This programming also permits selection of the time interval for recording analyte data, and allows the microprocessor to perform high precision mathematical operations required to accurately calculate analyte concentration values on the basis of signals received from the fiber optic sensor signal conditioning electronics. The programming also allows the microprocessor to average over time the calculated analyte concentration values.

The Fiber Optic Sensor Signal Programming further includes loading programming which allows the microprocessor to receive processed data from the flow measuring programming so as to calculate the actual discharge volume of an analyte or target pollutant contained in a fluid effluent. Algorithms are included for performing precise mathematical functions whereby the concentration values of the analyte as measured by the fiber optic sensor programming are multiplied by then-existing flow rates as measured by the flow measuring programming to calculate the actual volume of the target pollutant discharged over a given period of time. It will be understood that, if desired, the apparatus may be operated such that only the flow measuring means and fiber optic sensor and related programming are actuated, without any sampling operations. Further, the apparatus can be modified to eliminate the sampling assembly and related programming where a user is interested in monitoring an analyte of interest and obtaining loading values thereof, without any need to collect samples.

Data Storage Memory

Having described the various types of programming provided in the program storage memory (EPROM) of the microprocessor, the data storage memory of the microprocessor will now be described with reference to FIGS. 12 and 13A–13C.

The data storage memory is preferably provided in the form of random access memory (RAM) which stores specific details of operation set by the user and records sampling data, fluid flow data, and analyte data, as described in detail below. The data storage memory (RAM) is backed-up by its own battery, e.g., a lithium battery, so that data will remain stored therein even when the overall power source of the apparatus is turned off. The stored data will thus remain available until a new sampling cycle is started.

The sampling program parameters to be input by the user via keypad 17 and stored in RAM include: program start and stop criteria, time and/or flow interval between samples, analyte level(s) for initiating the sampler program, size of the sample, container for sample storage, and rinse and fault conditions for intake conduit 9. These parameters are set out in the leftmost "User Command" column in FIG. 13A, under "Specify Sampler Program". The invention contemplates that the microprocessor be programmed to sequentially prompt the user (via display 18) to enter these and other desired parameters via keypad 17.

The analyte level(s) which the user inputs in response to the prompt "Set Analyte Level(s) to Initiate Sampler Program" is stored in RAM along with other user inputs, and provides the unique capability of instructing the apparatus to initiate sample collection on the basis of predetermined analyte level(s) as described in greater detail below.

The microprocessor is programmed such that data will be collected during execution of a fluid sampling program, and will be stored in RAM. Such data includes all programmed entries, the time and date of each collected sample, data relating to any failed attempts to collect fluid samples, volume collected, volume remaining, bottle number, and time remaining until the next sample. The analyte concentration, loading and averaging data calculated by the apparatus is also stored in RAM.

Figure 13A:
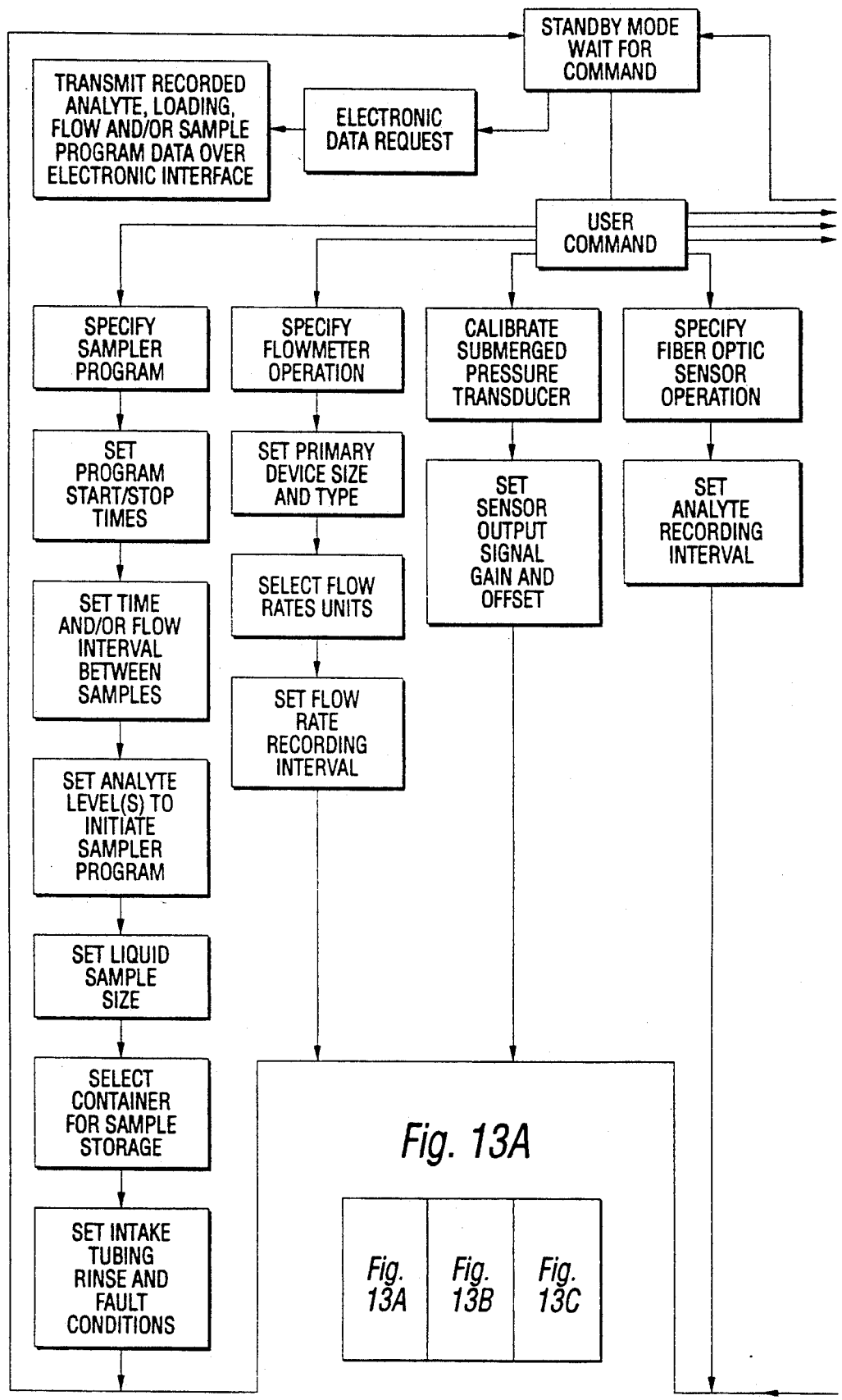
FIGS. 13A-13C together define a flow chart showing operational sequences of the apparatus according to various modes of operation selected by user commands.

In operation, the user first commands the apparatus, via keypad 17, to implement the "Specify Sampler Program" sequence (leftmost column in FIG. 13A). On receipt of this command the apparatus sequentially prompts the user, via alphanumeric display 18, to supply the details of the sampler program which is to be run. As the prompts sequentially appear on display 18, the user's responses are input through keypad 17. The most important information thus input by the user includes: time and date for the program to start and stop; number and size of fluid samples to be collected; time interval and/or quantity of fluid to pass the sampler between collected samples, and/or critical analyte level(s) to initiate and stop collection of fluid samples.

As depicted in the second column from the left in FIG. 13A, the user also commands the apparatus via keypad 17 to implement the "Specify Flowmeter Operation". On receipt of this command the user is prompted to input the primary device size and type, if any, the desired flow rate units, and the flow rate recording interval. As shown in the third column from the left in FIG. 13A, the user is also prompted to calibrate the flow sensor and set the sensor output signal gain and offset.

As depicted in the rightmost column in FIG. 13A, the user also commands the apparatus via keypad 17 to implement the "Specify Fiber Optic Sensor Operation". On receipt of this command, the user is prompted to set the interval at which analyte concentration will be measured and recorded.

Sampling, Analyzing and Monitoring Operations

When the user commands the apparatus via keypad 17 to "Execute Sampler/Flow Program" (FIG. 13B), sampling and flow measuring operations proceed without further instruction from the user. Fluid samples are collected on the basis of time and/or flow rate, and sampling and flow variables are automatically recorded, all on the basis of program parameters previously entered by the user.

Similarly, when the user commands the apparatus via keypad 17 to "Execute Sampler/Fiber Optic Sensor Program", sampling and analyte measuring operations proceed, without further instruction from the user. The apparatus will automatically measure and record analyte concentration values at time intervals previously entered by the user, and will automatically calculate and record analyte loading and averaging data.

Because the sampling and analyte monitoring capabilities of the apparatus are controlled by a common computer means, the apparatus provides the unique capability of permitting the user to instruct the apparatus to initiate sample collection on the basis of predetermined analyte or target pollutant level(s). Should an out-of-tolerance condition be detected during analyte monitoring operations by the fiber optic sensor, i.e., if the analyte concentration level falls outside a predetermined acceptable range set by the user, or above or below a given level set by the user, the apparatus will automatically initiate sample collection. By thus triggering sample collection on the basis of analyte level(s), the apparatus provides the unique capability of ensuring that samples are collected at critical times of upset in the process stream. In addition, by implementing only the triggering mode of operation, analytical costs can be reduced by limiting sample collection to upset conditions only, if desired.

In addition to sample collection triggered by critical analyte or target pollutant level(s), the apparatus is also capable of collecting samples on the basis of time and/or flow intervals as described above. It will be understood that the user is thus provided with a unique range of control over sample collection, and may instruct the apparatus to initiate the sampler program on the basis of any one or more of various desired modes of operation. As each new sampling cycle is started, the apparatus can be instructed to initiate the sampler program on the basis of time, flow or analyte level(s), or to simultaneously use all three parameters for controlling sample collection.

User Access to Stored Data

Figure 13B:
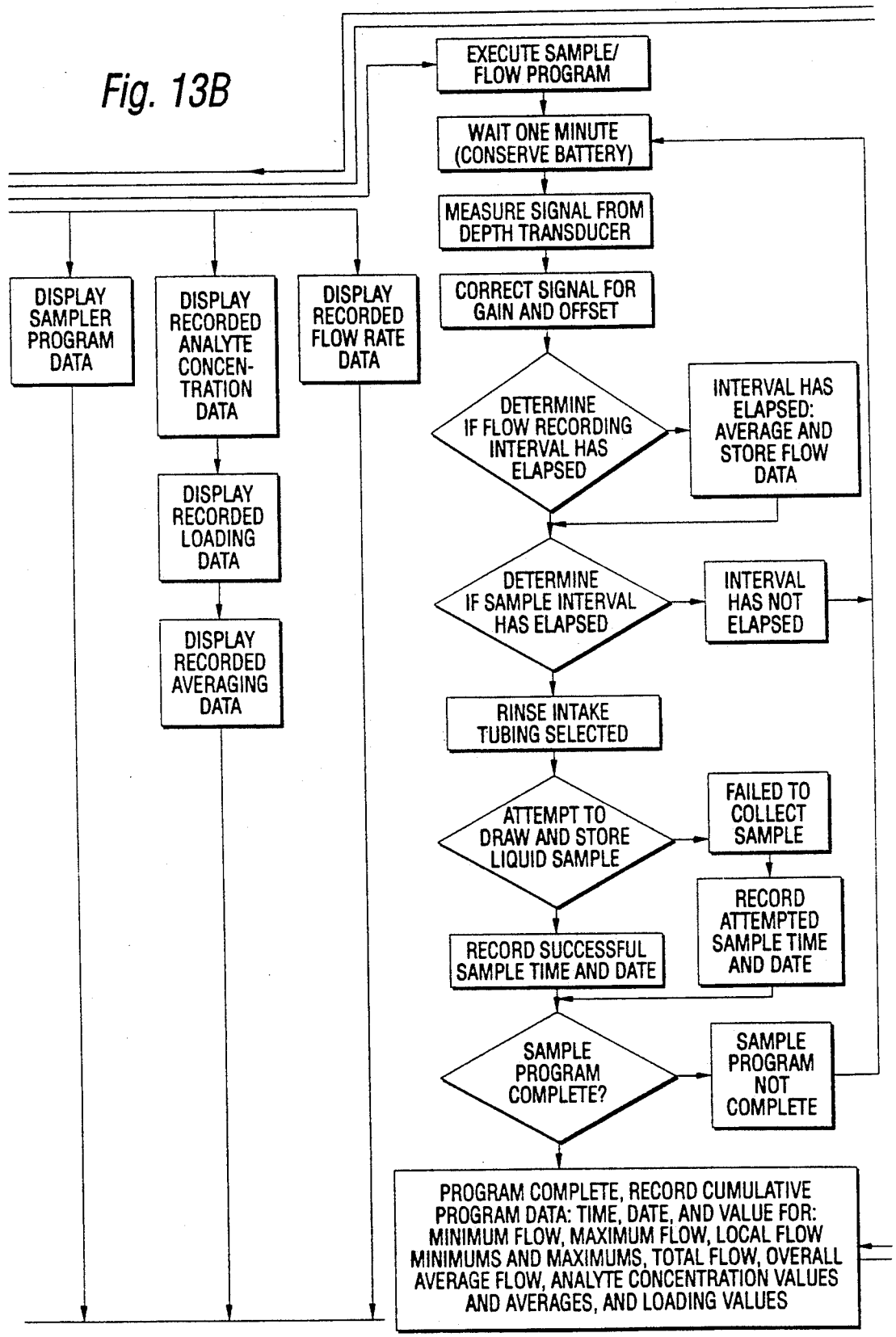
Figure 13C:
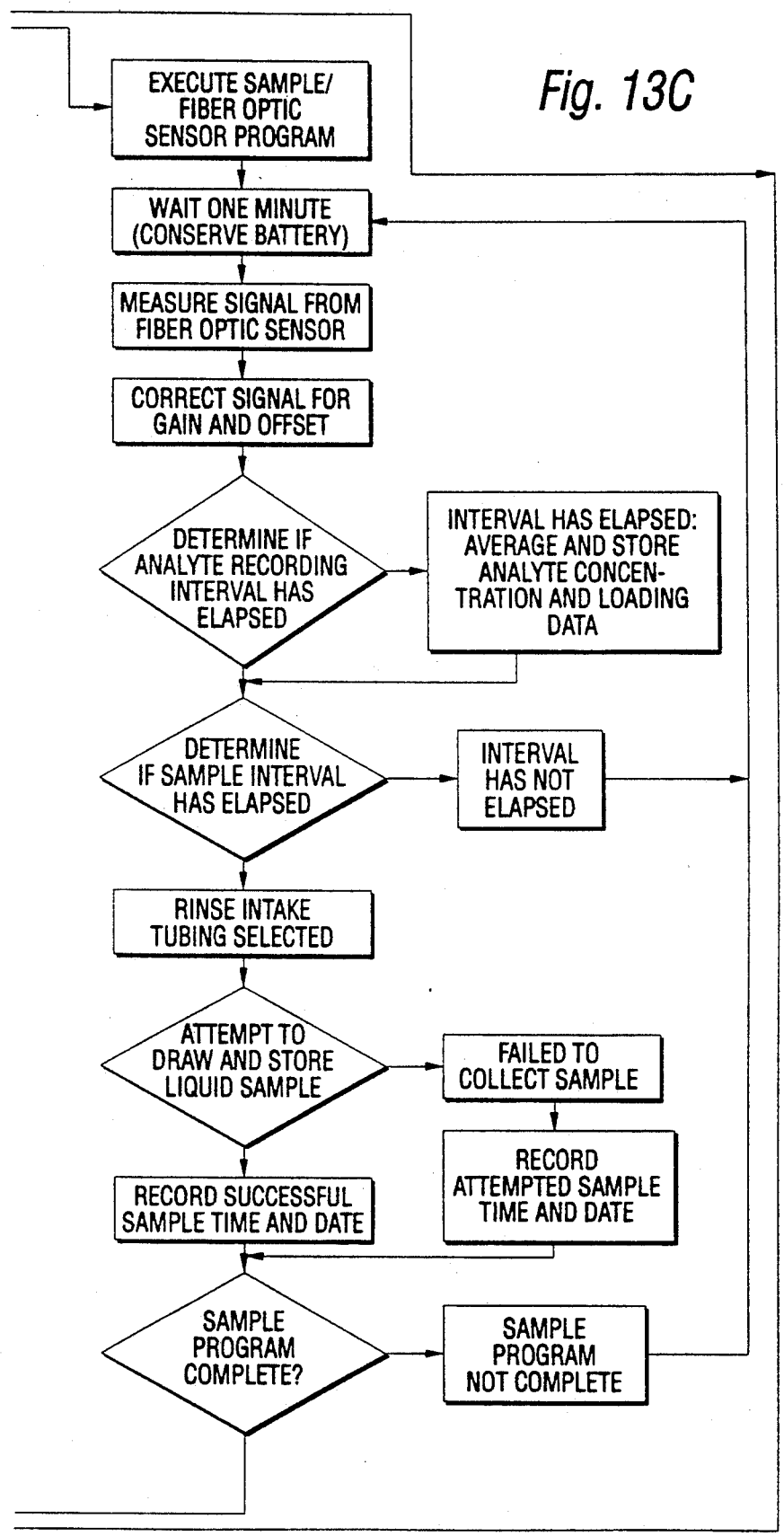

As depicted in the User Command section of FIGS. 13A and 13B, the user can request (via keypad 17) that the sampler program data; analyte concentration, loading or averaging data; and/or flow rate data stored in RAM be displayed on display 18 when desired. The sampler program display permits the user to review the details of the sampler program and real-time analyte monitoring operation previously specified by the user. The analyte data display provides the user with concentration, averaging and/or loading values recorded during the current or most recently completed sampler/fiber optic sensor program. Because the data storage memory comprises battery backed-up RAM, stored sampler program and analyte data will remain available for retrieval by the user until a "start" button is pressed to begin a new sampling cycle.

The invention provides an alternative means for retrieving stored sampler program, flow and analyte data in the form of a data transfer device, as indicated in the lowermost box of FIG. 12. The data transfer device can take one of various forms, as described below.

The data transfer device may comprise a portable data transfer unit which is preferably very compact, i.e., pocket-sized, so that the user can conveniently carry same for selective use. The portable data transfer unit is provided with its own microprocessor, the memory of which may take the form of CMOS RAM chips powered by a lithium battery (battery backed-up RAM). The unit is also preferably provided with a user-input keypad and an alphanumeric display, and resembles a conventional small pocket calculator in overall appearance. The unit is connected via a conventional connector cable (not shown) with one of the connectors 16, which may comprise a conventional 6-pin computer connector jack capable of a watertight connection. The user may then send an electronic data request command from the data transfer unit to the microprocessor of the apparatus. Upon receipt of such command, the microprocessor of the apparatus retrieves the requested data from its RAM and sends it for storage in the memory of the data transfer unit, via the connector 16.

When it is desired to retrieve the data thus stored in the data transfer unit, the unit is in turn connected, via a standard computer or printer jack for example, to an external output device (FIG. 12) in the form of a conventional printer or computer (e.g., a personal computer). The stored data can be read out directly on a printer to produce a hard copy thereof, with the microprocessor of the data transfer unit itself operating the printer in a known manner. The user is thus able to obtain a complete and accurate hard copy record of the data. Alternatively, the stored data can be transferred from the unit to a conventional computer for manipulation using an available software program for statistical analyses, spreadsheeting, etc.; for more permanent storage in a database stored in the computer's memory; and/or for printing by a printer connected to the computer.

Although it may not often be practical, the external connector 16 described above can alternatively be directly linked to a remote computer for direct transfer of the stored data if and when the apparatus itself is transported into close proximity with a computer. Alternatively, the external connector 16 can be directly linked, on-site, to a lap-top or notebook-type portable computer, and with the use of known communication software, stored data from the microprocessor can be transferred to the portable computer.

In accordance with another embodiment of the invention, the data transfer device may comprise a conventional modem, provided internally in the apparatus, or externally, so that stored data from the microprocessor can be transferred via a telecommunication network, such as a cellular telephone network, to a remote external output device. In this embodiment, the real-time, in situ monitoring capability of the fiber optic sensor, in combination with the substantially instantaneous transmission of data, enables a municipal engineer or other user to monitor analyte concentrations and loadings in a fluid discharge on substantially a real-time basis at a remote off-site location. This embodiment further permits central remote collection of data from a number of apparatus at various locations, via the telecommunication network, and long-distance re-programming of the program storage memory of each apparatus, as necessary.

The apparatus according to the invention may be adapted to monitor a number of different analytes, and to trigger sampler program operation on the basis of any desired one(s) of such analytes, depending upon the type of fiber optic sensor employed. The fiber optic sensor interface electronics and programming may be modified as necessary, depending upon the particular fiber optic sensor to be used. To this end, the program storage memory in the form of pre-installed EPROM chips may be programmed to perform the calculations necessary for a variety of different analytes. As such, the program storage memory can be programmed to have a relatively universal capacity capable of processing inputs from a variety of different sensors. Accordingly, the sensor 20 as described above can comprise a plurality of different fiber optic sensors responsive to different analytes of interest, so that in effect the sensor 20 serves as an in situ mini-lab capable of monitoring a number of different target pollutants or other analytes of interest, such as pH, biochemical oxygen demand, and the like.

The unique capability of the invention to provide actual loading data, i.e., of measuring the actual quantity of an analyte discharged into a receiving body or of averaging the values of a given analyte over time, is not restricted to use of a fiber optic sensor. For measuring the discharged quantity of an analyte, any type of sensor capable of providing in situ real-time measurement of an analyte may be employed as the sensor 20, such as, for example, a sensor for detecting total petroleum hydrocarbon. Suitable interface means and signal programming, comparable to that described above for the fiber optic sensor, may be provided to accommodate any such sensor, so that measured values of the analyte may be multiplied by then-existing flow rates as measured by the flow measuring programming to calculate the actual volume of the analyte discharged over a given period of time. Various types of sensors other than fiber optic sensors are also suitable for averaging purposes, such as a pH electrode station described in the aforementioned U.S. Pat. No. 5,172,332, the disclosure of which is incorporated herein by reference thereto.

In use, the apparatus according to the invention can be conveniently transported for use in any desired application. When used in a sewer manhole, the apparatus can be conveniently mounted as a single unitary structure above an open flowing sewer passage. The apparatus is mounted for use by: connecting the sensor 20 and the flow sensor with respective ones of the connectors 16; connecting the fluid intake conduit 9 with the pump 8; appropriately mounting the sensors relative to the fluid in the channel; positioning the weighted strainer 12 at the end of conduit 9 within the fluid in the channel; and suspending the unit from the upper end of the manhole. The integral unit includes all the electronics, computer programming, and hardware required for fully automatic sampling, real-time analyte monitoring, calculating loading data, and storage of sampling and analyte data for later retrieval.

It will be further understood that the apparatus of the invention may be selectively employed for use for sampling and analyte monitoring both, for sampling only, or for monitoring one or more analytes only, as desired. The independent implementation of either the sampling assembly or the analyte monitoring modes can be effected via user input to the computer control means according to the invention.

By virtue of the in situ, real-time monitoring capability of the fiber optic sensor, in certain applications it may be desirable to eliminate sampling operations entirely. It will be understood that the apparatus can be modified to eliminate the automatic sampling assembly and related programming, if desired. Such a modified apparatus would retain the full capabilities of monitoring and recording flow rate and analyte concentrations, averages and loadings, and data transfer capabilities.

While there have been described hereinabove what are at present considered to be the preferred embodiments of the invention, it will be understood that modifications may be made therein without departing from the spirit and scope of the invention. The present embodiments are therefore to be considered as illustrative, and not restrictive. The scope of the invention is indicated by the appended claims rather than by the foregoing description.

We claim:

1. An apparatus for automatically collecting samples from a fluid stream and for monitoring at least one analyte on a real-time basis, according to at least one mode of operation selected by a user, comprising:
   means for controlling said apparatus;
   a fluid sampling assembly having an inlet for receiving fluid from a fluid stream;
   power means for supplying power to said apparatus;
   said fluid sampling assembly, said control means and said power means comprising an integral operating unit;
   a fiber optic sensor for detecting values of said analyte in said fluid stream and for outputting signals related thereto, said fiber optic sensor being selectively connected to said integral operating unit; and
   said control means comprising a microprocessor, program memory and data memory, wherein:
   said program memory stores at least one equation for computing values of said analyte;
   said microprocessor receives said signals related to said analyte from said fiber optic sensor and utilizes said program memory to calculate values of said analyte based on said signals;
   said at least one mode of operation which may be selected by the user includes a first mode of operation in which sampling is triggered by at least one predetermined value of said analyte being monitored;
   said data memory stores user-selected input parameters including operating mode selection data and said at least one predetermined value of said analyte;
   said microprocessor controls said fluid sampling assembly according to said at least one mode of operation selected by the user, based on a deviation of computed values of said analyte from said user-selected predetermined value of said analyte; and
   said data memory stores fluid sampling data and analyte data.

2. An apparatus according to claim 1, wherein:
   said integral operating unit is disposed in a single case and comprises means for displaying said stored fluid sampling data and fluid condition data, said display means comprising an alphanumeric display mounted to said case so as to be visible to a user; and
   said apparatus further comprises user keypad means, mounted to said case and communicating with said data memory, for entering said user-selected input parameters and for retrieving said data stored in said data memory by a user commmand to display said data on said alphanumeric display.

3. An apparatus according to claim 1, wherein:
   said user-selected input parameters further comprise program start and stop criteria, fluid sample size, sample container selection, and intervals and units for storing analyte data.

4. An apparatus according to claim 1, wherein:
   said microprocessor automatically initiates fluid sample collection by said fluid sampling assembly when a present calculated value of said analyte deviates from said at least one predetermined value of said analyte by exceeding a predetermined value.

5. An apparatus according to claim 1, wherein:
   said microprocessor automatically initiates fluid sampling collection by said fluid sampling assembly when a present calculated value of said analyte deviates from said at least one predetermined value of said analyte by falling below a predetermined value.

6. An apparatus according to claim 1, wherein:
   said at least one predetermined value of said analyte comprises a pair of values defining an acceptable range for said analyte; and
   said microprocessor automatically initiates fluid sample collection by said fluid sampling assembly when a present calculated value of said analyte is outside said acceptable range of values of said analyte.

7. An apparatus according to claim 1, further comprising:
   a fluid sample intake conduit which extends to fluid in said stream, said sample intake conduit being selectively connectable to said fluid sampling assembly inlet; and
   said user-selected input parameters further comprising data relating to the volume of said sample intake conduit and purging thereof.

8. An apparatus according to claim 1, wherein:
   said program memory is programmed to average over time said calculated values of said analyte.

9. An apparatus according to claim 1, further comprising:
   means for selectively transferring said stored data to an external output device, said transfer means being controlled by said microprocessor.

10. An apparatus according to claim 9, wherein:
    said data transfer means comprises a modem operatively connected with said integral operating unit and disposed within said case, said modem being adapted to transfer data stored in said data memory via a telecommunication network to a remote external output device.

11. An apparatus according to claim 1, wherein said fiber optic sensor comprises:
    a light-transmission fiber optic core substantially surrounded by a clad, said core and clad together defining a fiber optic element;
    said clad being made of a material having a lower index of refraction than the index of refraction of said core;
    a light source operatively disposed relative to a light-receiving portion of said fiber optic element so as to input light thereto;
    detecting means, operatively arranged relative to said fiber optic element, for detecting changes in the transmission of light from said light source through said fiber optic element; and
    means for controlling light in said clad, whereby light from said fiber optic core which is incident on said detecting means is substantially unaffected by independent light propagation in said clad.

12. An apparatus according to claim 11, wherein:
    said light-controlling means comprises field stop means, disposed at said light-receiving portion of said fiber optic element, for obstructing light from said light source to said clad.

13. An apparatus according to claim 12, wherein:
    said light source comprises an LED; and
    said system further comprises aperture stop means, disposed between said LED and said light-receiving portion of said fiber optic element, so as to control the input of light from said LED to said fiber optic core.

14. An apparatus according to claim 13, wherein:
said field stop means and said aperture stop means are formed as a unitary element.

15. An apparatus according to claim 13, wherein:
said aperture stop means is provided with a central aperture having a diameter which is substantially less than the diameter of said fiber optic core.

16. An apparatus according to claim 11, wherein:
said light-controlling means comprises a clad light stop diaphragm disposed between a light-emitting portion of said fiber optic element and said detecting means.

17. An apparatus according to claim 1, wherein:
said at least one mode of operation includes a second mode of operation in which sampling is initiated on the basis of time;
said user-selected input parameters stored by said data memory include sampling times; and
said microprocessor controls said fluid sampling assembly according to said second mode of operation on the basis of said user input sampling times.

18. An apparatus according to claim 17, further comprising:
flow sensing means for outputting signals related to fluid flow in said stream, said sensing means being selectively connected to an input connection of said integral operating unit;
said program memory being programmed for computing values of a fluid flow-related variable;
said user-selected input parameters stored by said data memory includes at least one fluid flow-related parameter;
said microprocessor receives said signals related to fluid flow via said input connection and utilizes said program memory to calculate values of said fluid flow-related variable based on said signals and said at least one fluid flow-related parameter;
said at least one mode of operation includes a third mode of operation in which sampling is initiated on the basis of flow rate;
said microprocessor controls said fluid sampling assembly according to said third mode of operation on the basis of flow rate; and
said data memory stores fluid flow-related data.

19. An apparatus according to claim 18, further adapted to measure the actual discharge volume of said analyte loaded from said fluid stream into a receiving fluid body, wherein:
said program memory is programmed for computing flow rate values, and for calculating loading values on the basis of said analyte values and flow rate values;
said microprocessor receives said signals related fluid flow via said input connection and utilizes said program memory to calculate said flow rate values;
said microprocessor utilizes said program memory to calculate loading values of said analyte on the basis of said calculated analyte values and said flow rate values; and
said data memory stores loading data.

20. An apparatus according to claim 1, wherein:
said at least one mode of operation includes a second mode of operation in which sampling is initiated on the basis of time;
said user-selected input parameters stored by said data memory include sampling times; and
said microprocessor controls said fluid sampling assembly according to said second mode of operation on the basis of said user input sampling times.

21. An apparatus according to claim 20, wherein:
said at least one mode of operation includes a third mode of operation in which sampling is initiated on the basis of flow rate; and
said microprocessor controls said fluid sampling assembly according to said third mode of operation on the basis of flow rate as calculated by said program memory.

22. An apparatus for monitoring at least one analyte in a fluid discharge on a real-time basis, and for measuring an actual discharge volume of the analyte loaded from the fluid discharge into a receiving fluid body, comprising;
means for controlling said apparatus;
power means for supplying power to said apparatus;
said control means and said power means comprising an integral operating unit;
flow sensing means for outputting signals related to the flow rate of a fluid discharge, said flow sensing means being connected to said integral operating unit;
a sensor for detecting, in situ, said analyte in said discharge and for outputting signals related thereto, said sensor being connected to said integral operating unit; and
said control means comprising a microprocessor, program memory and data memory, wherein:
said program memory stores equations for calculating values of said analyte and flow rate values, and for calculating loading values on the basis of said analyte values and flow rate values;
said microprocessor receives said signal related to flow rate from said flow sensing means and utilizes said program memory to calculate the flow rate of said discharge;
said microprocessor receives said signals related to said analyte from said sensor and utilizes said program memory to calculate concentration values of said analyte based on said signals;
said microprocessor utilizes said program memory to calculate loading values of said analyte on the basis of said calculated analyte concentration values and flow rate values; and
said data memory stores analyte data, flow rate data and loading data.

23. An apparatus according to claim 22, further comprising:
a fluid sampling assembly having an inlet for receiving fluid from said fluid discharge, said fluid sampling assembly comprising part of said integral operating unit disposed within said case; and wherein
said apparatus is adapted to automatically collect samples from said fluid discharge according to at least one mode of operation selected by a user;
said at least one mode of operation which may be selected by the user includes a first mode of operation in which sampling is triggered by at least one predetermined value of said analyte being monitored;
said data memory stores user-selected input parameters including operating mode selection data and said at least one predetermined value of said analyte;

said microprocessor controls said fluid sampling assembly according to said first mode of operation, based on a deviation of computed values of said analyte from said user-selected predetermined value of said analyte; and said data memory stores fluid sampling data.

24. An apparatus according to claim 22, wherein said sensor comprises a fiber optic sensor comprising:

a light-transmissive fiber optic core substantially surrounded by a clad, said core and clad together defining a fiber optic element;

said clad being made of a material having a lower index of refraction than the index of retraction of said core;

a light source operatively disposed relative to a light-receiving portion of said fiber optic element so as to input light thereto;

detecting means, operatively arranged relative to said fiber optic element, for detecting changes in the transmission of light from said light source through said fiber optic element; and means for controlling light in said clad, whereby light from said fiber optic core which is incident on said detecting means is substantially unaffected by independently light propagation in said clad.

25. An apparatus according to claim 22, wherein:

said program memory is programmed to average over time said calculated values of said analyte.

26. An apparatus according to claim 22, further comprising:

means for selectively transferring said stored data to an external output device, said transfer means being controlled by said microprocessor.

27. An apparatus according to claim 26, wherein:

said data transfer means comprises a modem operatively connected with said integral operating unit and disposed within said case, said modem being adapted to transfer data stored in said data memory via a telecommunication network to a remote external output device.

28. An apparatus for automatically collecting samples from a fluid stream and for monitoring at least one analyte on a real-time basis, according to at least one mode of operation selected by a user, comprising:

means for controlling said apparatus;

a fluid sampling assembly having an inlet for receiving fluid from a fluid stream;

power means for supplying power to said apparatus;

said fluid sampling assembly, said control means and said power means comprising an integral operating unit;

a fiber optic sensor for detecting values of said analyte in said fluid stream and for outputting signals related thereto, said fiber optic sensor being selectively connected to said integral operating unit; and said control means comprising a microprocessor, program memory and data memory, wherein:

said program memory stores at least one equation for computing values of said analyte;

said microprocessor receives said signals related to said analyte from said fiber optic sensor and utilizes said program memory to calculate values of said analyte based on said signals;

said at least one mode of operation which may be selected by the user includes a first mode of operation in which sampling is initiated on the basis of time; and said data memory stores user-selected input parameters including operating mode selection data and sampling times, and further stores fluid sampling data and analyte data.

29. An apparatus according to claim 28, wherein:

said at least one mode of operation includes a second mode of operation in which sampling is triggered by at least one predetermined value of said analyte being monitored;

said data memory stores at least one predetermined value of said analyte selected by a user; and said microprocessor controls said fluid sampling assembly, in said second mode of operation, based on a deviation of computed values of said analyte from said user-selected predetermined value of said analyte.

30. An apparatus according to claim 29, further comprising:

flow sensing means for outputting signals related to fluid flow in said stream, said sensing means being selectively connected to an input connection of said integral operating unit;

said program memory being programmed for computing values of a fluid flow-related variable;

said user-selected input parameters stored by said data memory includes at least one fluid flow-related parameter;

said microprocessor receives said signals related to fluid flow via said input connection and utilizes said program memory to calculate values of said fluid flow-related variable based on said signals and said at least one fluid flow-related parameter;

said at least one mode of operation includes a third mode of operation in which sampling is initiated on the basis of flow rate;

said microprocessor controls said fluid sampling assembly according to said third mode of operation on the basis of flow rate; and said data memory stores fluid flow-related data.

31. An apparatus according to claim 30, further adapted to measure the actual discharge volume of said analyte loaded from said fluid stream into a receiving fluid body, wherein:

said program memory is programmed for computing flow rate values, and for calculating loading values on the basis of said analyte values and flow rate values;

said microprocessor receives said signals related to fluid flow via said input connection and utilizes said program memory to calculate said flow rate values;

said microprocessor utilizes said program memory to calculate loading values of said analyte on the basis of said calculated analyte values and said flow rate values; and said data memory stores loading data.

* * * * *

UNITED STATES PATENT AND TRADEMARK OFFICE
CERTIFICATE OF CORRECTION

PATENT NO.   : 5,299,141
DATED        : March 29, 1994
INVENTOR(S)  : Hungerford et al.

It is certified that error appears in the above-indentified patent and that said Letters Patent is hereby corrected as shown below:

Column 18, line 40 (claim 11, line 3), change "light-transmission" to --light-transmissive--.

Column 21, line 13 (claim 24, line 7), change "retraction" to --refraction--;
Column 21, line 25 (claim 24, line 19), change "pendently" to --pendent--.

Signed and Sealed this

Second Day of August, 1994

Attest:

BRUCE LEHMAN

*Attesting Officer*    *Commissioner of Patents and Trademarks*